United States Patent [19]

Masuda et al.

[11] Patent Number: 4,813,210
[45] Date of Patent: Mar. 21, 1989

[54] RADIATION-STERILIZED, PACKAGED MEDICAL DEVICE

[75] Inventors: Toshiaki Masuda, Ibaraki; Hitoshi Omiya, Shiga; Kiyoshi Fukui, Uji, all of Japan

[73] Assignee: Nissho Corporation, Osaka, Japan

[21] Appl. No.: 105,463

[22] Filed: Oct. 1, 1987

Related U.S. Application Data

[62] Division of Ser. No. 854,354, Apr. 21, 1986, abandoned.

[30] Foreign Application Priority Data

Sep. 27, 1985 [JP] Japan .................. 60-214350

[51] Int. Cl.⁴ .................. B65B 55/08; B65B 55/16; B65B 31/02
[52] U.S. Cl. .................. 53/425; 53/434; 53/449; 53/472
[58] Field of Search .................. 53/425, 426, 449, 434, 53/469, 472, 512

[56] References Cited

U.S. PATENT DOCUMENTS

| 2,746,193 | 5/1956 | Billian | 53/425 X |
| 3,618,283 | 11/1971 | Moore et al. | 53/425 X |
| 3,726,057 | 4/1973 | Kemble | 53/425 |
| 3,815,315 | 6/1974 | Glick | 53/434 X |
| 3,850,084 | 11/1974 | Fowler et al. | 53/449 X |
| 4,022,324 | 5/1977 | Schuster | 53/425 X |
| 4,035,981 | 7/1977 | Braun et al. | 53/426 |
| 4,223,512 | 9/1980 | Buchner | 53/425 |
| 4,603,538 | 8/1986 | Shave | 53/434 X |

FOREIGN PATENT DOCUMENTS 58-134840  8/1983  Japan .

Primary Examiner—Horace M. Culver
Attorney, Agent, or Firm—Armstrong, Nikaido, Marmelstein & Kubovcik

[57] ABSTRACT

A packaged medical device comprising a medical device; a gas-permeable sterile bag containing the medical device therein; a wrapping member made of oxygen-impermeable material and wherein said medical device-containing bag, previously subjected to radiation-sterilization, is sealed; and a deoxidizing agent contained in the wrapping member together with the medical device-containing bag. The packaged medical device does not give off an odor upon unsealing and is free from decrease in strength of plastic parts thereof.

9 Claims, 1 Drawing Sheet

RADIATION-STERILIZED, PACKAGED MEDICAL DEVICE

This application is a division of application Ser. No. 854,354 filed Apr. 21, 1986 and now abandoned.

BACKGROUND OF THE INVENTION

The present invention relates to a radiation-sterilized medical device. More particularly, the present invention relates to a packaged medical device provided with a deodorizing means adapted to prevent emanation of an odor upon withdrawal of a radiation-sterilized medical device from a sterile containment bag.

As a method for sterilizing medical devices, sterilization with gamma-rays has been widely employed in recent years, particularly in the field of disposable medical devices. In order to maintain sterility up till the time of use, such a disposable medical device is generally sealed in a sterile bag and then sterilized with gamma-rays as pre-packaged in the bag. However, because of the presence of oxygen in the bag, irradiation with gamma-rays or other radiation excites the oxygen to yield ozone, an allotrope of oxygen, and, hence, generates the so-called gamma odor which is considered to be associated with ozone. This odor emanating upon unsealing of the sterile bag for removal of the medical device therefrom gives an uncomfortable sensation to the user of the device.

Furthermore, disposable medical devices are made, for the most part, of some plastic material or other and may suffer from decreased strength due to oxidation with time. Particularly in dry radiation-sterilization in a gaseous atmosphere where the surface of the plastic material is exposed to air, the presence of radiation-excited oxygen promotes oxidation of the plastic material with time at elevated temperature so as to induce a decrease in strength.

In view of the problems mentioned hereinbefore, the present inventors conducted an intensive research and discovered that these problems all spring out from the presence of oxygen. Accordingly, they sought for means for elimination of oxygen.

The object of the present invention is to provide a dry radiation-sterilized medical equipment which does not give off an odor upon unsealing and is free from decreases in the strength of plastic parts thereof.

This and other objects of the invention will become apparent from the description hereinafter.

SUMMARY OF THE INVENTION

The present invention provides a packaged medical device comprising a medical device; a gas-permeable sterile bag containing the medical device therein; a wrapping member made of oxygen-impermeable material and wherein said madical device-containing bag, previously subjected to radiation-sterilization, is sealed; and deoxidizing agent contained in the wrapping . member together with the medical device-containing bag.

DETAILED DESCRIPTION

Figure 1:
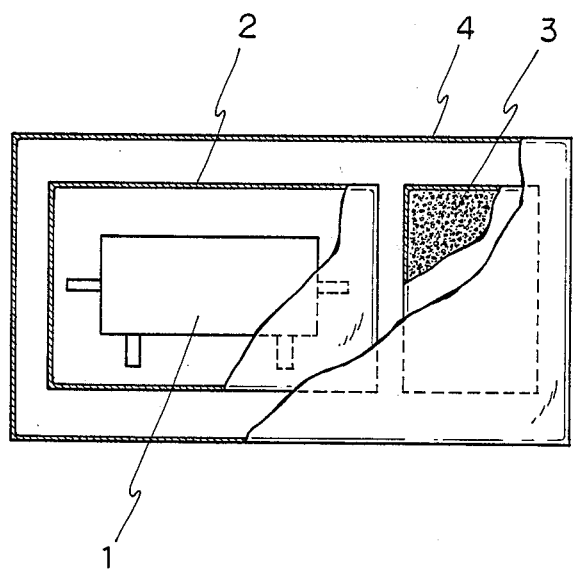
FIG. 1 is a schematic illustration showing a packaged medical device in accordance with the present invention.

In the present invention, the radiation-sterilization is preferably sterilization with gamma-rays and the deoxidizing agent is preferably one based on activated iron oxide. The medical device to which the present invention can be applied with advantage includes a hollow fiber blood processing device, particularly a blood processing device employing a cellulose acetate hollow fiber membrane, which is generally believed to be incompatible with dry radiation-sterilization. The oxygen-impermeable material is preferably a laminated polyester-aluminum-polyethylene sheet.

According to the present invention, a medical device sealed in a sterile bag, after radiation-sterilization, is hermetically sealed in a wrapping member of oxygen-impermeable material together with a deoxidizing agent. For the reason, there is substantially no infiltration of oxygen from external environments and even the oxygen trapped in the course of the wrapping step is absorbed by the co-existing deoxidizing agent. Therefore, the inside of the wrapping member can be maintained in anoxic state so that the emanation of an odor and aging of the strength of the medical device can be successfully prevented.

Furthermore, since the sterile bag is a gas-permeable sterile bag, the oxygen and ozone present in the bag and the oxygen gradually released from the medical device are also instantly absorbed.

In addition, since the wrapping member is made of an oxygen-impermeable material, the entry of oxygen from the external environment is prevented almost completely and, therefore, an oxygen-free condition within the wrapping member can be maintained for a long time period.

An preferred embodiment of the present invention will now be described with reference to the accompanying drawing.

Referring to FIG. 1, a packaged medical device according to the present invention comprises a medical. device 1 such as hollow fiber blood processing device, as sealed in a sterile bag 2 and further hermetically sealed, together with a deoxidizing agent 3, in a wrapping member 4. That is, the medical device 1 as such is first sealed in the sterile bag 2 and, then, after sterilization with gamma-rays, hermetically sealed into the wrapping member 4 together with the deoxidizing agent 3.

The sterile bag 2 is a gas-permeable sterile bag and the wrapping member 4 is made of an oxygen impermeable material. The reason for using such a gas-permeable bag as the sterile bag is that if a gas-impermeable sterile bag be employed, even if sealing is made under oxygen-free conditions, the oxygen inherent in the medical device itself is gradually released and collects within the sterile bag and, as experience tells, the decrease in strength of the medical device is accelerated at elevated temperature.

In the invention, the term "sterile bag" is intended to mean a bag which is subjected to sterilization treatment in a state that a medical device is contained therein and through the wall of which bacteria cannot pass. The sterile bag may be gas-permeable over the entire surfaces thereof or in a part thereof.

Examples of the sterile bag include the followings: (1) A bag, both sides of which are made of a laminated polyester-polyethylene film and which has one or more gas-permeable parts where one or more openings such as slit are provided in the laminated film and the opening portions are covered with a polyethylene nonwoven fabric or a wood-free paper. (2) A bag, one side of which is made of a wood-free paper or a polyethylene non-woven fabric, and the other side of which is made of a laminated polyester-polyethylene film. (3) A bag, both sides of which are made of a wood-free paper or a polyethylene non-woven fabric.

The reason for using a wrapping member made of an oxygen-impermeable material is to prevent infiltration of oxygen from external environments and, hence, to ensure a long efficacy life of the deoxidizing agent. Examples of the wrapping member used in the invention include a laminated sheet consisting of an exterior polyester film, an intermediate aluminum foil (or aluminum deposition layer) and an inner polyethylene film, a laminated sheet consisting of an exterior polyester film, an intermediate polyethylene film, an intermediate aluminum foil (or aluminum deposition layer) and an inner polyethylene film, a laminated sheet consisting of an exterior biaxially orientated polypropylene film, an intermediate ethylene-vinyl alcohol copolymer film and an inner polyethylene film, a laminated sheet consisting of an exterior vinylon film having a polyvinylidene chloride coating on both sides thereof and an inner polyethylene film, a laminated sheet consisting of an exterior biaxially orientated polyvinyl alcohol film and an inner polyethylene film, a laminated sheet consisting of an exterior polyvinylidene chloride-coated orientated polypropylene film and an inner polyethylene film, a laminated sheet consisting of an exterior polyvinylidene chloride-coated polyester film and an inner polyethylene film, a laminated sheet consisting of an exterior polyvinylidene chloride-coated oriented nylon film and an inner polyethylene film, a laminated sheet consisting of an exterior polyvinylidene chloride-coated cellophane and an inner polyethylene film, and a laminated sheet consisting of an exterior laminated high impact polystyrene-polyvinylidene chloride-polyethylene film and an inner non-oriented polypropylene film. From the standpoint of cost and efficiency, the most preferred examples of the oxygen-impermeable materials are a laminated sheet consisting of an exterior polyester film, an intermediate aluminum foil (or aluminum deposition layer) and an inner polyethylene film, and a laminated sheet consisting of an exterior polyester film, an intermediate polyethylene film, an intermediate aluminum foil (or aluminum deposition layer) and an inner polyethylene film.

The sterilization method may be any radiation-sterilization method, including one using gamma-rays and one utilizing electron beams. However, the present invention is more effective in case of sterilization with gamma-rays, which has a greater influence on the strength of the medical device, since the effect of the present invention which comprises sealing a medical device in an oxygen-impermeable wrapping member together with a deoxidizing agent is noticeably exhibited, especially when the problem of decreased strength of the medical device due to radiation-excited oxygen is taken into consideration.

The absorbed dose used in the radiation-sterilization sterilization varies depending upon the kind of medical device and the kind of radiation. In the case of sterilization of hollow fiber blood processing device with gamma-rays, an absorbed dose of 1.8 to 2.5 Mrad is usually used.

Because the deoxidizing agent is sealed together with a medical device contained in a gas-permeable sterile bag, it must be non-toxic. Moreover, the deoxidizing agent is preferably one which does not give rise to gases (hydrogen gas, carbon dioxide gas, and the like) upon absorption of oxygen. For these reasons, the deoxidizing agent is desirably one based on an active metal or metal compound and having its reaction rate, etc. controlled by a catalyst. The active metal or metal compound may for example be iron, zinc, copper or tin, or oxides of the foregoing metal but among the currently available deoxidizing agents, those based on activated iron oxide are most desirable. Among commercial deoxidizing agents of this type is Ageless (a commercial name of Mitsubishi Gas Chemical Company, Inc.). The deoxidizing agent is contained in a gas-permeable bag or container.

In the present invention, it is essential that, the medical device-containing bag is previously sterilized and then sealed together with a deoxidizing agent in an oxygen-impermeable wrapping member. That is, it must be avoided that a medical device is sealed together with a deoxidizing agent in a gas-impermeable bag and is subjected to radiation-sterilization in a state that the deoxidizing agent is present in the bag. The reason therefor is that when the medical device-containing bag is subjected to radiation sterilization in a state that a deoxidizing agent is present in the bag, the D value (which means the absorbed dose in which the number of bacteria is reduced to one-tenth time that before irradiation) is increased. This tendency is marked particularly in the case of a medical device using cellulose acetate hollow fiber, as shown in Example 4. The tendency is also observed in the case of a medical device using silicone rubber hollow fiber.

As a method for removing the odor generated within the sterile bag, it might be contemplated to seal active carbon as a deodorant together with the medical device but in view of the fact that this material occupies more than 10 times the volume of a typical deoxidizing agent, that its deodorizing efficiency is poor at elevated temperature, and that it does not prevent the decrease of strength with time, for instance, the use of active carbon is not suitable for the purposes of the present invention.

Referring to the medical device to be packed according to the present invention, the method for inhibiting decrease of strength in accordance with the present invention, that is a method comprising sealing a medical device contained in a gas-permeable sterile bag in an oxygen-impermeable wrapping member together with a deoxidizing agent after radiation-sterilization, can be applied to the radiation-sterilization of any medical device basically made of a plastic material. For example, the present invention is of course effective for a medical device such that its loss of strength will be confined within a tolerable range even without provision of any specific means for preventing such decrease of strength. However, from the standpoint of cost and efficiency, the present invention can be preferably applied to hollow fiber blood processing devices, particularly to blood processing devices employing cellulose acetate hollow fiber membranes. Typical example of hollow fiber blood processing devices includes dialyzer for artificial kidney. The present invention is also preferably applied to artificial lung employing silicone rubber hollow fiber membranes and to catheter made of silicone rubber.

The present invention is more specifically described and explained by means of the following Examples. It is to be understood that the present invention is not limited to the Examples, and various change and modifications may be made in the invention without departing from the spirit and scope thereof.

EXAMPLE 1

A dialyzer containing a bundle of 8,800 cellulose acetate hollow fibers each having an effective length of 20 cm, an outer diameter of 230 μm and an inner diameter of 200 μm was placed in a gas-permeable sterile bag, both sides of which was made of a laminated polyester-polyethylene film and which had a slit on the one side thereof with the slit portion being covered with a polyethylene non-woven fabric, and the bag was sealed. The bag containing the dialyzer was sterilized by irradiation of gamma-rays in a dose of 2.5 Mrad. The sterilized bag was inserted together with 10 g of Ageless as a deoxidizing agent into a wrapping member in the form of bag and made from a laminated sheet consisting of a polyester film having a thickness of 12 μm, an aluminum foil having a thickness of 9 μm and a polyethylene film having a thickness of 40 μm, which layers were laminated in that order, and the wrapping member was heat-sealed.

The deodorizing effect was determined at appropriate time intervals. The results are shown in Table 1. In Table 1, 1W, 2W and 4W represent the storage periods of 1, 2 and 4 weeks, respectively. The symbols in Table 1 mean the followings:

No odor is detected.
Odor is detected.

EXAMPLE 2

The same procedures as in Example 1 were repeated except that a laminated sheet consisting of a polyester film having a thickness of 12 μm, a polyethylene film having a thickness of 15 μm, an aluminum foil having a thickness of 9 μm and a polyethylene film having a thickness of 40 μm, which layers were laminated in that order, was used as a wrapping member.

The results are shown in Table 1.

COMPARATIVE EXAMPLES 1 AND 2

The same procedures as in Example 1 were repeated except that 50 g of an active carbon was used instead of Ageless (Comparative Example 1) or both Ageless and the active carbon were not used (Comparative Example 2).

The results are shown in Table 1.

TABLE 1

| Storage condition | | Blank (no irradiation) | Irradiation (2.5 Mrad) | | | |
|---|---|---|---|---|---|---|
| Temp. (°C.) | period | | Ex. 1 | Ex. 2 | Com. Ex. 1 | Com. Ex. 2 |
| 40 | 1 W | | | | | X |
| | 2 W | | | | | X |
| | 4 W | | | X | | X |
| 50 | 1 W | | | | | X |
| | 2 W | | | X | | X |
| | 4 W | | | X | | X |
| 60 | 1 W | | | X | | X |
| | 2 W | | | X | | X |
| | 4 W | | | X | | X |

The results of Table 1 reveal that the use of a deoxidizing agent produces a noticeable deodorizing effect.

EXAMPLE 3

The same hollow fiber as used in Example 1 was sterilized and packaged in the same manner as in Example 1. The aging of the strength of the follow fiber was determined. The results are shown in Table 2. In Table 2, each strength value is expressed in terms of an average value + standard deviation for ten hollow fibers.

COMPARATIVE EXAMPLE 3

The same procedures as in Example 3 were repeated except that no deoxidizing agent was used. The results are shown in Table 2.

TABLE 2

| Storage condition | | Blank (No irradiation) | | Irradiation (2.5 Mrad) | | | |
|---|---|---|---|---|---|---|---|
| | | | | Ex. 3 | | Com. Ex. 3 | |
| Temp. (°C.) | Period | Tensile strength at breaking (g/fiber) | Elongation at breaking (%) | Tensile strength at breaking (g/fiber) | Elongation at breaking (%) | Tensile strength at breaking (g/fiber) | Elongation at breaking (%) |
| 40 | 1 W | 76 ± 13 | 80 ± 11 | 76 ± 10 | 82 ± 13 | 75 ± 6 | 81 ± 12 |
| | 2 W | 78 ± 10 | 81 ± 10 | 77 ± 8 | 79 ± 8 | 61 ± 8 | 73 ± 10 |
| | 4 W | 77 ± 11 | 79 ± 12 | 77 ± 10 | 80 ± 10 | 55 ± 7 | 72 ± 14 |
| 50 | 1 W | 78 ± 12 | 80 ± 10 | 77 ± 8 | 80 ± 12 | 70 ± 5 | 75 ± 8 |
| | 2 W | 77 ± 11 | 79 ± 13 | 78 ± 6 | 81 ± 10 | 58 ± 7 | 72 ± 13 |
| | 4 W | 79 ± 10 | 79 ± 7 | 76 ± 10 | 79 ± 12 | 49 ± 8 | 70 ± 10 |
| 60 | 1 W | 78 ± 12 | 80 ± 10 | 76 ± 12 | 79 ± 9 | 58 ± 7 | 73 ± 8 |
| | 2 W | 76 ± 10 | 80 ± 6 | 76 ± 8 | 80 ± 12 | 42 ± 5 | 67 ± 10 |
| | 4 W | 77 ± 15 | 79 ± 11 | 75 ± 10 | 79 ± 8 | 31 ± 6 | 50 ± 12 |

The results of Table 2 reveal that the use of a deoxidizing agent contributes remarkably to prevention of decrease in strength due to aging from the hollow fiber.

EXAMPLE 4

The same dialyzer as used in Example 1 was placed in the same sterile bag as used in the Example 1 and gamma-rays were irradiated thereto. The D value was determined with respect to *Bacillus pumilus* ATCC 27142. The results are shown in Table 3.

The same procedures as in the above were repeated with a dialyzer using polypropylene hollow fibers or an artificial lung using silicone rubber hollow fibers. The results are also shown in Table 3.

COMPARATIVE EXAMPLE 4

The same procedures as in Example 4 were repeated except that each medical device was placed together with Ageless in the same oxygen-impermeable wrapping member as used in Example 1 and then subjected to irradiation of gamma-rays. The results are shown in Table 3.

TABLE 3

| Hollow fiber | D value (Mrad) | |
| --- | --- | --- |
|  | Ex. 4 | Com. Ex. 4 |
| Cellulose acetate | 0.213 | 0.405 |
| Polypropylene | 0.197 | 0.210 |
| Silicone rubber | 0.167 | 0.258 |

Results of Table 3 reveal that the irradiation of gamma-rays in the presence of a dioxidizing agent invites a great increase in the D value, particularly in the case of cellulose acetate hollow fiber. Therefore, it is desirable that the irradiation of gamma-rays is carried out in the absence of a dioxidizing agent.

In addition to the elements and ingredients used in the Examples, other elements and ingredients can be used in the Examples as set forth in the specification to obtain substantially the same results.

It will be apparent from the foregoing description that since the present invention comprises sealing a medical device contained in a gas-permeable sterile bag further in an oxygen-impermeable wrapping member together with a deoxidizing agent, it eliminates the oxygen from the wrapping member as well as from the sterile bag and even disposes of the oxygen emanating gradually from the medical device as well.

Furthermore, since the wrapping member is made of an oxygen-impermeable material, there is substantially no entry of external oxygen so that the deoxidizing agent may retain its function for an extended time period.

What we claim is:

1. A process for producing a radiation-sterilized medical device comprising the steps of:
    placing a medical device within a gas-permeable sterile bag;
    sealing said gas-permeable sterile bag;
    sterilizing said gas-permeable sterile bag containing said medical device by gamma rays;
    placing said sterilized gas-permeable bag containing said medical device and also placing a deoxidizing agent within an oxygen impermeable wrapping member; and
    sealing said oxygen-impermeable wrapping member.

2. A process of producing a radiation-sterilized medical device according to claim 1, wherein said sterilizing is medical device according to claim 1, wherein said sterilizing is conducted by dry radiation-sterilizing in a gaseous atmosphere.

3. A process of producing a radiation-sterilized medical device according to claim 1, wherein said deoxidizing agent is based upon activated iron oxide.

4. A process of producing a radiation-sterilized medical device according to claim 1, wherein said medical device is a hollow fiber blood processing device.

5. A process of producing a radiation-sterilized medical device according to claim 4, wherein said hollow fiber blood processing device is a dialyzer containing cellulose acetate hollow fibers.

6. A process of producing a radiation-sterilized medical device according to claim 4, wherein said hollow fiber blood processing device is an artificial lung containing silicone rubber hollow fibers.

7. A process of producing a radiation-sterilized medical device according to claim 1, wherein said medical device is a catheter made of a silicone rubber.

8. A process of producing a radiation-sterilized medical device according to claim 1, wherein said oxygen-layer-aluminum layer-polyethylene layer.

9. A process of producing a radiation-sterilized medical device according to claim 1, wherein said oxygen-impermeable wrapping member is made of a laminated polyester layer-polyethylen layer-aluminum layer-polyethylene layer.

* * * * *